(12) United States Patent
Owen-Simonson

(10) Patent No.: US 10,159,698 B2
(45) Date of Patent: Dec. 25, 2018

(54) TOPICAL SKIN HEALING SALVE

(76) Inventor: Bobbie Michelle Owen-Simonson, Fresno, CA (US)

( * ) Notice: Subject to any disclaimer, the term of this patent is extended or adjusted under 35 U.S.C. 154(b) by 0 days.

(21) Appl. No.: 13/495,334

(22) Filed: Jun. 13, 2012

(65) Prior Publication Data

US 2018/0236008 A1     Aug. 23, 2018

(51) Int. Cl.

| | | |
|---|---|---|
| *A61K 35/644* | (2015.01) | |
| *A61K 9/06* | (2006.01) | |
| *A61P 31/04* | (2006.01) | |
| *A61P 17/02* | (2006.01) | |
| *A61K 9/00* | (2006.01) | |

(52) U.S. Cl.
CPC .......... *A61K 35/644* (2013.01); *A61K 9/0014* (2013.01); *A61K 9/06* (2013.01); *A61P 17/02* (2018.01); *A61P 31/04* (2018.01)

(58) Field of Classification Search
None
See application file for complete search history.

(56) References Cited

U.S. PATENT DOCUMENTS

| | | |
|---|---|---|
| 5,270,042 A | 12/1993 | Whitham |
| 5,518,722 A | 5/1996 | Szaloki et al. |
| 6,017,551 A | 1/2000 | Riley |
| 6,406,721 B1 | 6/2002 | Owens et al. |
| 6,576,269 B1 | 6/2003 | Korneyev |
| 6,844,014 B1 | 1/2005 | Rafkin |
| 7,357,950 B2 | 4/2008 | Mazzio et al. |
| 7,666,451 B2 | 2/2010 | Mazzio et al. |
| 7,691,419 B2 | 4/2010 | DiLeva |
| 8,021,700 B1 | 9/2011 | Johnson |

*Primary Examiner* — Susan Hoffman

(74) *Attorney, Agent, or Firm* — Richard A. Ryan

(57) ABSTRACT

A topical skin healing salve and method of making the same for treating and healing a wide variety of injuries, ailments and other skin conditions. The salve of the present invention comprises beeswax, white petroleum jelly or said castor bean jelly, unprocessed honeycomb or honey, yellow dock root, yellow dock leaves, marigold and/or calendula leaves, plantain weed and chickweed. The method of the present invention melts the beeswax, petroleum or castor bean jelly and honeycomb and/or honey. The other ingredients are added to the mixture and the combination is simmered to leach out the beneficial qualities thereof. The mixture is strained and placed in containers to cool and solidify. The salve has healing, pain relieving, anti-inflammatory, antiseptic, antibacterial properties and is water resistant and resistant to being easily washed or scraped off. The petroleum or castor bean jelly softens the skin to improve active ingredient interaction with the damaged skin.

14 Claims, 3 Drawing Sheets

TOPICAL SKIN HEALING SALVE

BACKGROUND OF THE INVENTION

A. Field of the Invention

The present invention relates generally to salves, ointments and other compositions for the treatment of human skin. More specifically, the present invention relates to topical treatment salves that are utilized as a first aid ointment to beneficially treat burned, inflamed or irritated human skin, including injuries resulting from cuts, scrapes, stings and bites, and skin conditions such as eczema and psoriasis. Even more particularly, the present invention relates to such topical skin treatment salves where the active ingredients are primarily derived from natural ingredients such as weeds, herbs and honey.

B. Background

Topical salves, ointments and other compositions that are configured and utilized for healing injuries to the human skin and for the treatment of various skin conditions are well known in the art. For purposes of the present invention, all such topical skin treating compositions are collectively referred to herein as salves. Presently available salves are generally comprised of familiar, expected and readily available ingredients that are selected for their individual and/or their combined skin healing and treating features. Although the use of salves to heal and treat the human skin have been known for many years, there is an ever present need for an improved topical skin treating salve that provides healing and treating benefits that are heretofore not accomplished by existing salves.

Because skin is the largest organ on the human body and the part of the body that is most exposed to the environment and, as a result, most subject to injury, it is the part of the body which is most frequently in need of treatment to resolve injuries. As well known, injuries to the human skin can result from animal or plant scratches, cuts from tools, branches or other persons, burns from hot liquids or surfaces, sunburns from over-exposure to the sun, wind burns, damage from exposure to excessive cold temperature, rashes from exposure to plants and a wide variety of allergens, stings from insects and spiders, and bites from animals, spiders and the like. Injuries to the human skin are also known to result from scrapes against rough surfaces, such as a carpets, rugs, rocks, sand and the like. A wide variety of other injuries are also possible for the human skin. In addition to injuries, it is well known that the human skin is also very susceptible to a wide variety of different skin-specific ailments, including but not limited to eczema and psoriasis. Although some skin conditions only affect isolated areas of the skin and last for relatively short durations, many human skin ailments are known to be somewhat widespread and last for long durations, including for the person's lifetime. All such injuries, ailments and other skin conditions generally cause irritation and, in many instances, pain to the person who is suffering from the condition. In addition, such injuries, ailments and other conditions can disfigure the area of the skin subject to the condition. In some circumstances, the disfigurement resulting from an injury or skin condition can be a significant source of embarrassment to the person suffering from the injury or ailment. In more extreme cases, this embarrassment can cause the person to avoid physical contact with others, avoid going out of doors and/or completely covering up the affected area(s), if possible, at all times so the disfigurement cannot be seen by others.

Presently available salves for treating skin injuries, ailments and other conditions are at least primarily, and most often substantially, made from synthetically produced ingredients. There is a desire for topical skin treating salves that are made, at least primarily, from natural ingredients. Although the use of naturally produced ingredients, including those derived from plants, honey and the like, in salves is generally well known, most such salves are either too difficult or expensive to make, utilize materials which are either difficult to find or produce or do not satisfactorily treat many common injuries, ailments and other skin conditions. To beneficially be able to treat skin conditions, any salve must be configured with ingredients that can facilitate the active ingredients being sufficiently adsorbed into the skin so they can treat the injury, ailment or other condition. In addition, a beneficially configured salve should provide antiseptic qualities to facilitate healing and reduce the likelihood of infection. Further, in order to beneficially treat skin conditions, the salve should be configured to stay on the skin for a sufficient amount of time to accomplish its healing objectives. As well known, presently available salves generally do not provide these benefits.

What is needed, therefore, is an improved topical skin treating salve that is useful for beneficially treating a wide variety of skin injuries, ailments and conditions. The improved skin treating salve would be configured to be absorbed into the human skin in a manner that allows the active ingredients of the salve to fully interact with the person's skin so the treating properties of the various active ingredients can treat the skin. Preferably, an improved topical skin treating salve will be made, at least primarily, from natural ingredients, particularly the active ingredients of the salve. The ingredients for an improved topical skin treating salve should be at least generally readily available so the cost of the salve is not price prohibitive and so the salve can be manufactured in sufficient quantities so as to be commercially produced and made widely available.

SUMMARY OF THE INVENTION

The topical skin healing salve of the present invention solves the problems and provides the benefits identified above. That is to say, the present invention discloses a skin healing salve which is topically applied to a person's skin so as to treat the skin for injuries, ailments and other skin conditions. The topical skin healing salve of the present invention is able to beneficially treat a wide range of skin injuries, ailments and other conditions, including such skin conditions as psoriasis and eczema. The active ingredients of the present topical skin healing salve are natural ingredients that are specifically selected so as to work together to heal and treat skin that has been injured or which suffers from a variety of different ailments. The salve of the present invention also comprises ingredients which soften the skin so as to facilitate absorption into the area of the skin where treatment is desired so the active ingredients of the salve can interact with the skin and provide the desired treatment thereof. The active ingredients of the topical skin healing salve of the present invention are generally well known, though not heretofore having been combined in the manner set forth herein, and readily available so as to enable the salve to be manufactured in a cost efficient manner and be widely distributed for sale.

In one general aspect of the present invention, the topical skin healing salve comprises one-half (0.5) pound of raw beeswax that is preferably cut into cubes, twenty-six (26) ounces plain white petroleum jelly, two (2) to three (3) tablespoons of raw unprocessed honeycomb and/or honey, one and one-half (1½) teaspoons of finely chopped dried yellow dock root, six (6) to seven (7) crumpled dried yellow dock leaves that are each approximately seven (7) to eight (8) inches long, one (1) cup or eight (8) ounces of firmly packed dried marigold and/or calendula leaves, one (1) cup or eight (8) ounces of firmly packed dried plantain weed, and one (1) cup or eight (8) ounces of firmly packed dried chickweed. In an alternative embodiment, the white petroleum jelly is replaced with castor bean jelly to produce an organic version of the salve of the present invention. The raw beeswax, the white petroleum jelly or the castor bean jelly and the raw unprocessed honeycomb or honey are heated in a cooking container until melted to a mixture. In a preferred embodiment, the cooking container is a double boiler. Once these ingredients are fully melted and still hot (but not too hot), the yellow dock root, yellow dock leaves, marigold and/or calendula leaves, plantain weed and chickweed are added to the mixture in the cooking container. The heat is turned down to a medium-low heat and the combined mixture is allowed to simmer for a minimum of sixty minutes or longer so allow all of the valuable healing properties of the plants into the mixture. The mixture is strained to remove plant material and other debris therefrom and then poured into one or more product containers to cool and solidify for distribution as the salve.

In another general aspect, the method of the present invention comprises the following steps: (a) placing a mixture comprising one-half (0.5) pound raw beeswax, twenty-six (26) ounces plain white petroleum jelly or castor bean jelly and two (2) to three (3) tablespoons of raw unprocessed honeycomb and/or honey into a cooking container; (b) applying heat to the mixture until the mixture is melted; (c) turning down the heat to a medium-low heat and adding to the mixture one and one-half (1½) teaspoons of dried yellow dock root, six (6) to seven (7) dried yellow dock leaves each being approximately seven (7) to eight (8) inches long, one (1) cup or eight (8) ounces of dried marigold and/or calendula leaves, one (1) cup or eight (8) ounces of dried plantain weed, and one (1) cup or eight (8) ounces of dried chickweed; (d) cooking, preferably by allowing the mixture to simmer, the mixture for at least sixty minutes; (e) straining the mixture to remove debris; and (f) pouring the mixture into one or more product containers to cool and solidify so it may be distributed as salve. In the preferred embodiment of the method, the cooking container is a double broiler, the yellow dock root is finely chopped, each of the marigold or the calendula, the plantain weed and the chickweed are firmly packed and the yellow dock leaves are crumpled in the adding step. If desired, fresh plant material may be utilized instead of the dried plant material. As will be readily appreciated by those skilled in the art, fresh plant material is not as potent as dried plant material, which is typically more concentrated than the fresh plant material. If fresh plant material is used, each of the plant material quantities should be approximately doubled. As will be noted by persons familiar with plants, the pant materials utilized for the salve of the present invention are weeds that can grow practically everywhere, making the salve extremely cost effective to produce.

Accordingly, the primary objective of the present invention is to provide a topical skin healing salve that provides the advantages discussed above and which overcomes the disadvantages and limitations associated with presently available topical skin treating salves.

It is also an important object of the present invention to provide a topical skin healing salve in which the active ingredients thereof are primarily comprised of natural ingredients, such as weeds, herbs, flowers and honey, that are selected for their ability to heal the skin and prevent infection at the injured area thereof.

It is also an important object of the present invention to provide a topical skin healing salve that is applied to a person's skin so as to treat the skin for injuries, ailments and other skin conditions, including injuries such as burns, cuts, scrapes, stings, bites and the like and diseases such as eczema, psoriasis and the like, while reducing the pain associated with such conditions.

It is also an important object of the present invention to provide a topical skin healing salve that has ingredients which are selected so as to soften the skin and facilitate absorption of the active ingredients into the area of the skin where treatment is desired so the active ingredients can interact with the skin and provide the desired treatment thereof It is also an important object of the present invention to provide a topical skin healing salve that has ingredients which are selected to aid in the healing of the skin and prevention of infection and which provide a consistency that is generally thick and water-resistant so the salve can be utilized without a bandage, will not melt off of hot, infected skin and will not be easily washed or scraped off of the treated area.

It is also an important object of the present invention to provide a topical skin healing salve that generally comprises a mixture of yellow dock roots and leaves, marigold and/or calendula leaves and/or flowers, plantain weed, chickweed and honeycomb and/or honey as the active ingredients and raw bee's wax and white paraffin petroleum jelly, or castor bean jelly for an all natural salve, as the base ingredients.

Another important object of the present invention to provide a topical skin healing salve in which the active ingredients thereof are well known to persons skilled in the art of plants and natural products produced therefrom, widely available and easy to grow so as to enable the salve to be manufactured in a cost efficient manner and be widely distributed for sale.

The above and other objectives of the present invention will be explained in greater detail by reference to the attached figures and the description of the preferred embodiment which follows. As set forth herein, the present invention resides in the novel features of form, construction, mode of operation and combination of processes presently described and understood by the claims.

BRIEF DESCRIPTION OF THE DRAWINGS

In the drawings which illustrate the preferred embodiments and the best modes presently contemplated for carrying out the present invention.

DETAILED DESCRIPTION OF THE PREFERRED EMBODIMENTS

Figure 1:
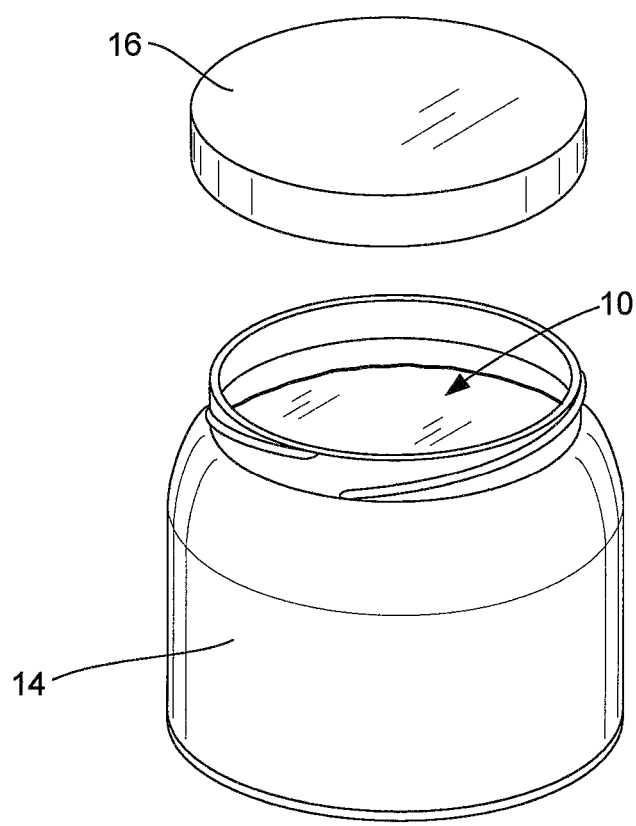
FIG. 1 is a side perspective view of a product container having a quantity of the topical skin healing salve of the present invention therein shown with the lid separated from the container.

With reference to the figures where like elements have been given like numerical designations to facilitate the reader's understanding of the present invention, the preferred embodiments of the present invention are set forth below. The enclosed text and drawings are merely illustrative of preferred embodiments and only represent several possible ways of configuring the present invention. Although specific components, materials, configurations and uses are illustrated, it should be understood that a number of variations to the components and to the configuration of those components described herein and in the accompanying figures can be made without changing the scope and function of the invention set forth herein. For instance, although the figures and the description set forth herein are primarily directed to a topical skin treating salve and a method of making the same using certain quantities of the ingredients thereof, persons skilled in the art will readily understand that this is merely for purposes of simplifying the present disclosure and that the present invention is not so limited. The method of making the topical skin treating salve and the salve resulting therefrom can be made in a variety of quantities A topical skin healing salve that is made from the ingredients and which is configured pursuant to one or more embodiments of the present invention is referred to as 10 in FIG. 1. A method of making the topical skin healing salve of the present invention is shown generally as 12 in FIGS. 2 and 3. As set forth in more detail below, the topical skin healing salve 10 of the present invention is made from a new and unique combination of certain specifically and specially selected weeds, herbs, honey and petroleum jelly, as set forth in the method 12 of FIG. 2. In an alternative embodiment, the topical skin healing salve 10 is made as an all-natural product by replacing the petroleum jelly with castor bean jelly, as shown in the method 12 of FIG. 3. These embodiments of the topical skin healing salve 10 are discussed in more detail below. The salve 10 of the present invention, made pursuant to the method 12, can be placed in a product container 14, such as a glass jar or the like, having a removable lid 16 that allows access to the salve 10 when needed, as shown in FIG. 1, and which encloses the salve 10 when not being utilized. As will be readily appreciated by those skilled in the art, the salve 10 of the present invention can be placed in a variety of different types of product containers 14 for use, distribution and storage of the salve 10.

Figure 2:
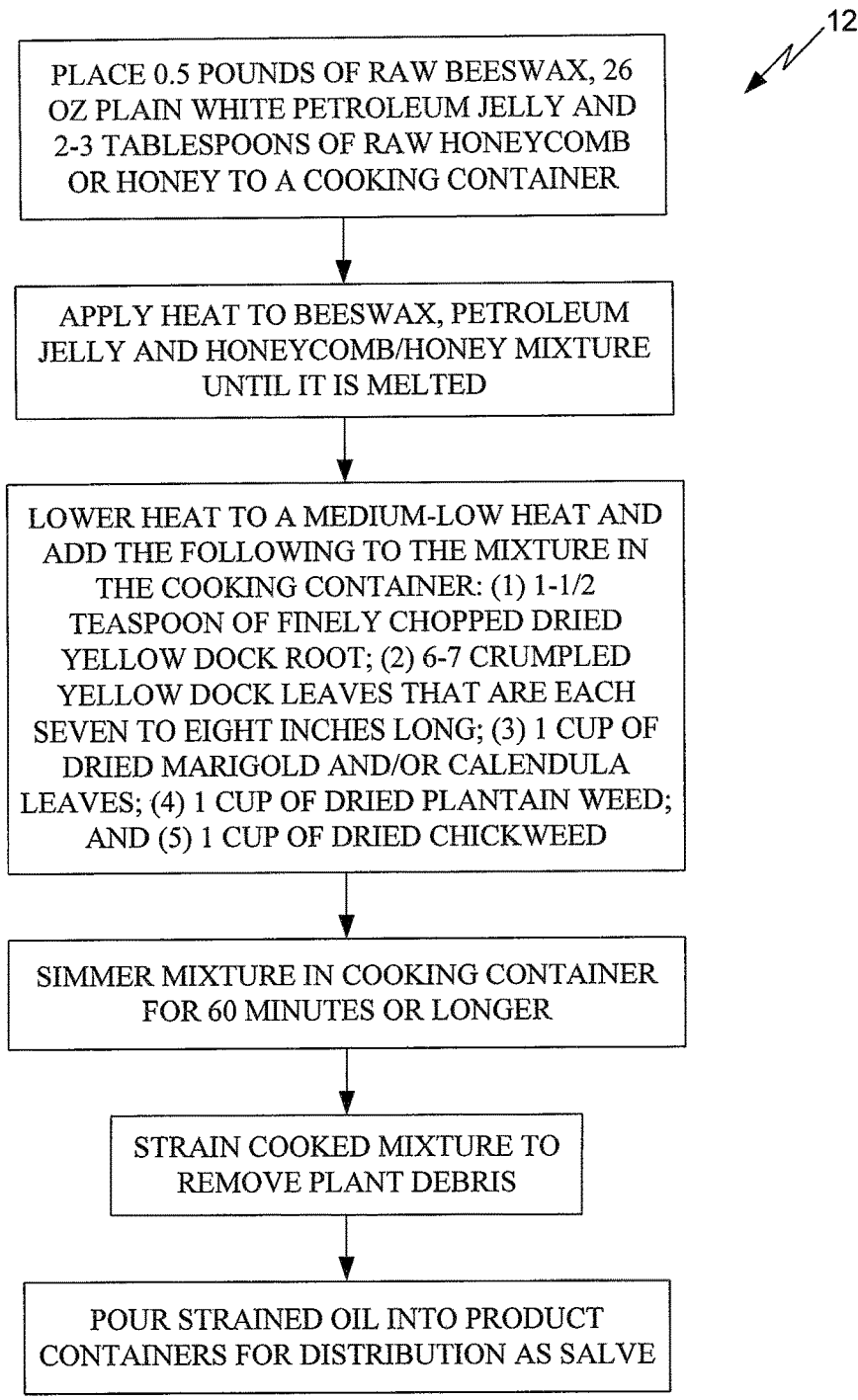
FIG. 2 is a schematic flow diagram of a method making a topical skin healing salve that is configured according to one of the preferred embodiments of the present invention using petroleum jelly.
Figure 3:
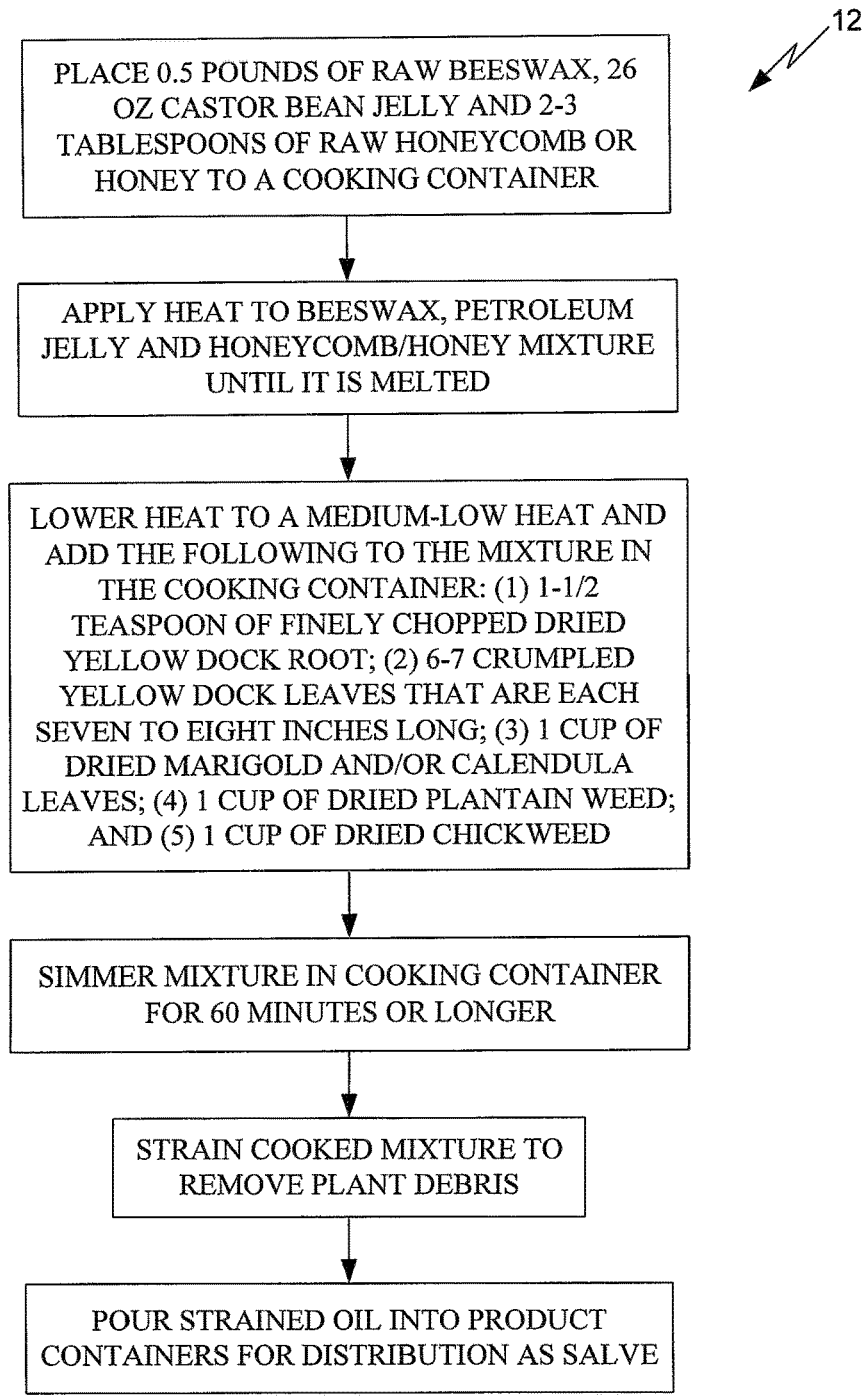
FIG. 3 is a schematic flow diagram of a method making a topical skin healing salve that is configured according to an alternative embodiment of the present invention using castor bean jelly.

As set forth in FIG. 2, in one embodiment of the topical skin healing salve 10 of the present invention generally comprises raw beeswax, plain white petroleum jelly, raw unprocessed honey and/or honeycomb, dried yellow dock root, yellow dock leaves, dried marigold and/or calendula leaves, dried plantain weed and chickweed. In the embodiment of FIG. 3, the plain white petroleum jelly is replaced with castor bean jelly to produce an all-natural, organic version of the topical skin healing salve 10 of the present invention. As will be appreciated by persons who are skilled in the relevant art, the herb ingredients of the topical skin healing salve 10 of the present invention are specifically chosen for their healing, anti-inflammatory, anti-septic, anti-bacterial and like characteristics and are combined with the healing, protective, infection fighting and pain relieving affects of the raw unprocessed honey, honeycomb and beeswax. The salve 10 of the present invention, produced according to the method 12, has a generally thick consistency and is water resistant so it can be utilize without having to cover it with a bandage or other covering. In addition, the salve 10 will not melt off of hot, infected skin or be easily washed or scraped off. Certain ingredients of the salve 10 of the present invention, namely the plain white petroleum jelly or castor bean jelly, are utilized to soften the skin where the salve 10 is applied so that the active, healing ingredients thereof will be quickly absorbed into the injured, sick or otherwise damaged skin to allow these active ingredients to immediately begin providing pain relief for the user and to begin healing the damaged skin.

One of the primary active ingredients of the salve 10 of the present invention is chickweed (*Stellaria media*). Although chickweed is native to Europe, it commonly grows across North America as a common weed. As with the other herbs utilized to produce the salve 10, the chickweed should be picked when it is its most succulent. Chickweed first emerges in the garden in the early spring. As well known in the art, chickweed is an annual herb and it has a high water content that relies on a soaking rain to stimulate its growth. In many temperate climates, chickweed even has a short revival in the fall after the autumn rains. Chickweed is commonly used as an external remedy for cuts, wounds and, perhaps most commonly, skin itching and irritation. In addition, chickweed is known to have powerful anti-inflammatory benefits. As a result of all of its beneficial properties, chickweed is a popular ingredient in herbal moisturizers that are configured to ease skin irritation issues associated with psoriasis and eczema. Chickweed is also utilized to heal rashes (including diaper rash), burns, chapped skin, insect bites, stings and other wounds. For the method 12 of the present invention, dried chickweed is utilized to make salve 10 and provide the skin-related benefits described above.

Another active ingredient for the salve 10 of the present invention is plantain weed (*Plantago major*), which is also known as the Common Plantain or Broad-leaved Plantain. Although plantain is believed to be indigenous to the Eurasia region, this perennial weed can be found almost anywhere in North America, having been brought here by early European settlers who value it for its culinary and medicinal properties, as well as across much of Europe. In general, plantain will typically grow in sun to shade conditions and in almost any type of soil. Because plantain is very adaptable and spreads by seeds, it is usually very plentiful. Plantain can be easily harvested anytime from early spring until frost. The plantain weed is well known as a healing agent for wounds and to provide a cooling affect to areas of the skin impacted by injuries, rashes and the like. Plantain is also known as an astringent, a substance which contracts the tissues or canals of the body, thereby diminishing discharges therefrom, such as blood or mucus. Plantain is also well known as a demulcent, an agent that forms a soothing film over a mucous membrane, thereby relieving minor pain and inflammation. The plantain weed is useful as a emollient, a complex mixtures of chemical agents that make the external layers of the skin softer, and a vulnerary, a plant whose extract is widely sued to soothe and heal skin. Plantain also has antimicrobial properties that kill or inhibit the growth of microorganisms such as bacteria and anti-toxin properties allowing it to form antibodies in response to biological toxins that are capable of neutralizing the toxins. In light of the above, plantain is well known as a herb that is useful for treating a wide variety of different ailments and injuries. With regard to the salve 10 of the present invention, plantain lessens the pain of stings, bites, scrapes and rashes. In addition, it also works to staunch blood flow and close wound edges. As with the chickweed, the plantain utilized for the salve 10 of the present invention should be harvested when it is at its most succulent. For the method 12 of the present invention, dried plantain weed is utilized to make salve 10 and provide the various skin-related benefits described above.

Another active ingredient for the salve 10 of the present invention is marigold and/or calendula flowers and/or leaves. The most commonly cultivated and used member of the genus is the pot marigold (*Calendula officinalis*). The marigold plant is an annual that originally was found in southern Europe and the eastern Mediterranean, but which now grows in many parts of North America. In general, the seeds for the marigold plant will germinate in almost any soil and will grow in sunny to half-sunny conditions. Plants sown in April will tend to flower in June and continue flowering until frost. The marigold herb is well known for its ability to sooth inflamation, control bleeding and heal damaged tissues. This herb has also been shown to stimulate the development of granulation tissue, which is the fibrous connective tissue that replaces a fibrin clot in healing wounds, where the skin is broken. The marigold flowers and leaves of the marigold herb, and/or the calendula, are commonly utilized to revitalize dry, red skin patches and as a natural remedy for the treatment of minor dermatological problems like epidermal sunburn, bruises, tiny lacerations, bumps and scratches. Since ancient times, calendula flowers have been used for skin infections and ulcers. Other well known skin-related uses of marigold/calendula flowers and/or leaves include use as an antiseptic and to reduce pain caused by wasp or bee stings. Lotion made from marigold and/or calendula is used by many people to help heal the painful lesions caused by dry eczema. As with the chickweed and the plantain weed, the marigold/calendula utilized for the salve 10 of the present invention should be harvested when it is at its most succulent. For the method 12 of the present invention, dried marigold and/or calendula flowers and/or leaves are utilized to make salve 10 and provide the skin-related benefits described above.

Other active ingredients for the salve 10 of the present invention are the leaves and root of yellow dock (*Rumex crispus*). This common "weed" is also native to Europe and Asia, but now grows throughout North America. In Europe, yellow dock is cultivated as a vegetable. For medicinal purposes, it is the root and leaves that are most commonly utilized. In ancient Roman days, yellow dock was used for a variety of skin complaints. Native Americans applied crushed leaves to boils and the pulverized roots to skin cuts. When the root is scraped, it has a deep yellow color, which matches its well-known name. The roots are typically eight to twelve inches long and about one-half inch thick. Yellow dock is applied externally as an antiseptic and an astringent. The leaves and root of the yellow dock have been utilized for treating chronic skin complaints, especially psoriasis, skin cuts, swelling, rashes, acne, boils, burns, bleeding, hemorrhoids, dog and insect bites and wounds. The roots of the yellow dock herb are dug in late summer and autumn, typically between the months of August and October, and are prepared by being cleaned well, split lengthwise and then dried. The dried roots of the yellow dock herb are typically ground or crushed and then used to prepare ointments, tinctures, decoctions or teas. The ground/crushed root is kept cool and dry, but not frozen. For the salve 10 of the present invention, it is preferred that roots of a plant at least two years old be utilized and which were dug after autumn frosts or very early in the spring. Yellow dock leaves can be harvested any time. As with chickweed, plantain weed and marigold/calendula, the yellow dock utilized for salve 10 of the present invention should be harvested when it is at its most succulent. For the method 12 of the present invention, dried yellow dock root and leaves are utilized to make salve 10 and provide the various skin-related benefits described above.

Another ingredient of the topical skin healing salve 10 of the present invention is raw unprocessed honey. As well known, raw honey is the purest, healthiest and most nutritious form of honey and is considered by some to be one of the most beneficial and natural substances on earth. Unlike clean and clear processed honey, raw honey looks milkier and contains particles therein, such as bits of honeycomb, broken bee wings and pollen. The benefits of raw honey for use with skin conditions, as well as other ailments, are attributed to its antibiotic, antifungal, antiseptic and antibacterial properties. As such, raw honey is used for treating cuts, burns, skin rashes, skin ulcers and wounds. Raw honey reduces swelling, controls infections and promotes healing by acting as a protective barrier over the wound. In one use, the application of raw honey two to three times a day on the affected area of the skin stimulates growth and repairs damaged tissue. In one embodiment of the salve 10 and method 12 of the present invention, the inventor herein utilized raw, unprocessed honey from the Cornett Farms in Dinuba, Calif. to and provide the various skin-related benefits described above.

Raw unprocessed honeycomb and beeswax are also utilized in the method 12 to produce the salve 10 of the present invention. As with the raw, unprocessed honey, raw unprocessed honeycomb and beeswax are utilized for their healing properties. In addition, the raw unprocessed honeycomb and beeswax are also utilized for their water resistant effects and as an ingredient thickener and skin softener. In one embodiment of the salve 10 and method 12 of the present invention, the inventor utilized raw, unprocessed honeycomb and beeswax from the Cornett Farms in Dinuba, Calif.

In one embodiment, shown in the method 12 of FIG. 2, plain white paraffin or petroleum jelly is also utilized to make the topical skin healing salve 10 of the present invention. The petroleum jelly is utilized because of its ability to quickly and deeply soften the skin, which ensures the optimum penetration of all of the active ingredients of salve 10 set forth above so these active ingredients may interact with the skin and provide the desired healing thereof. This ability to quickly and deeply soften the skin allows the salve 10 to be quickly effective for multiple first aid and healing purposes. Plain white paraffin or petroleum jelly is readily available from numerous retail and wholesale outlets. As will be readily appreciated by those skilled in the art, the paraffin/petroleum jelly is the only ingredient that prevents salve 10 from being completely organic. In an alternative embodiment, shown with regard to the method 12 set forth in FIG. 3, castor bean jelly can be utilized instead of the paraffin/petroleum jelly to provide an all organic salve 10. Castor bean jelly is produced from castor beans and is generally slicker than the paraffin/petroleum jelly and, as a result, is easier to spread. However, it does not tend to soften the skin as quickly and deeply as the paraffin/petroleum jelly and, as a result, does not provide the fast, deep penetration of the salve's active ingredients that can generally be best achieved by the paraffin/petroleum jelly (which is preferred unless an organic product is desired).

Although the various ingredients for the topical skin healing salve 10 of the present invention are generally well known, they have not heretofore been combined in the manner set forth in the method 12 to produce the salve 10 of the present invention. Through trial and error, the present inventor has found that the mixture of these ingredients in the various amounts set forth in the method hereof produces a new and unique salve 10 that is very beneficial for healing skin which has been injured, affected or otherwise damaged by a wide variety of different types of injuries, ailments and conditions. Among other benefits, the salve 10 has healing, pain relieving, anti-inflammatory, antiseptic, antibacterial properties and is generally water resistant and resistant to being easily washed or scraped off. Example uses of salve 10, in addition to various other uses described herein, include applying the salve 10 to babies and small children with diaper rash, raw skin around the nose, mouth and etc., to nursing mothers who have cracked and bloody nipples from nursing a child, and to reduce the pain and inflammation that is associated with hemorrhoids. The salve 10 can also be utilized on dogs, cats, rats, pigs and guinea pigs (although the area where the salve 10 is to be applied may have to be shaved first), as the salve 10 does not contain any toxic materials that could harm the animal if they lick it off.

One method 12 of making the salve 10, summarized in FIG. 2, includes the step of placing one-half pound of raw beeswax cut into cubes, 26 ounces of plain white petroleum jelly and two to three heaping tablespoons of raw honeycomb or honey in a cooking container, such as a double boiler or the like, and then applying heat to the beeswax, petroleum jelly and honeycomb/honey mixture until the mixture melts. In the preferred embodiment, water is placed in the lower half of the double broiler, the above materials are placed in the upper half of the double broiler and the water in the lower half of the double boiler is heated to at or near boiling to completely melt the mixture in the upper half of the double broiler. Once the mixture is melted, the user turns down the heat to a medium-low heat and adds the following ingredients: (1) One and one-half teaspoon of finely chopped dried yellow dock root; (2) six to seven crumpled yellow dock leaves that are each seven to eight inches long; (3) one cup or eight ounces of firmly packed dried marigold and/or calendula leaves; (4) one cup or eight ounces of firmly packed dried plantain weed; and (5) one cup or eight ounces of firmly packed dried chickweed. The above mixture is then cooked, by allowing it to simmer, for at least sixty minutes or longer. During the simmering step, the valuable healing properties of the plant materials are leached out into the mixture. The melted, cooked mixture is strained into a container, typically initially a container such as a glass measuring cup or the like, to get rid of the plant matter/debris in the mixture and then poured into a product container 14, such as the jar shown in FIG. 1, to cool and solidify and then be distributed as salve 10. Preferably, the user will try to squeeze as much oil from the plant matter as possible before straining the oil mixture to rid it of the plant matter and/or other debris. In the alternative embodiment of FIG. 3, the placing step is modified by replacing the petroleum jelly with a like amount of castor bean jelly to produce an organic version of the salve 10 of the present invention. As will be obvious to persons skilled in the art, the above-described quantities can be altered and still obtain the desired salve 10 and can be modified to achieve different quantities of the salve 10. For instance, if the desires to utilize fresh plant material (e.g., the plantain, yellow dock leaf and root, marigold and/or calendula leaves and chickweed) instead of dried plant material, the recipe for the salve 10 will need to be modified to utilize approximately double the amount of the subject plant material. As will be readily appreciated by those skilled in the art, fresh plant material is generally not as potent as dried plant material because it is not as concentrated and, therefore, more of the plant material will usually be necessary to produce salve 10.

The aforementioned salve 10 of the present invention is envisioned to be suitable for relatively large-scale production so as to be made generally available in locations wherever consumer skin care and first aid care products are sold, such as drug stores, grocery stores, convenience stores and the like. In use, the user of the salve 10 will first identify an area of the skin that is to be treated, which is typically where an injury, ailment or other condition exists. The user then removes a relatively small amount of the salve 10 from the product container 14 and applies the salve 10 to the affected skin area. The petroleum jelly or castor bean jelly will moisturize the skin enabling the active ingredients of the salve 10 to more efficiently and effectively penetrate into the skin so they will be able to better interact therewith to treat and heal the injured, sick or otherwise damaged skin. The active ingredients will immediately begin providing pain relief for the user and begin healing the damaged skin.

While there are shown and described herein one or more specific embodiments of the present invention, it will be readily apparent to those skilled in the art that the invention is not so limited, but is susceptible to various changes in quantities and materials without departing from the spirit and scope of the invention. The foregoing descriptions of specific embodiments of the present invention have been presented for purposes of illustration and description and are not intended to be exhaustive or to limit the scope of the invention to the precise forms disclosed. The above embodiments were set forth above for the purposes of best illustrating and explaining the principles of the present invention and one or more practical uses thereof so as to enable persons skilled in the art to best understand and utilize the present invention. Persons skilled in the art will readily understand and appreciate that they will be able to utilize the teachings of this disclosure to modify the present invention as may be necessary to suit their specific needs and/or requirements without departing from the spirit or scope of the claims of the present invention.

What is claimed is:
1. A topical skin healing salve, comprising:
one-half (0.5) pound raw beeswax;
twenty-six (26) ounces plain white petroleum jelly or castor bean jelly;
two (2) to three (3) tablespoons of raw unprocessed honeycomb and/or honey;
one and one-half (1½) teaspoons of dried yellow dock root;
six (6) to seven (7) dried yellow dock leaves, each of said yellow dock leaves being approximately seven (7) to eight (8) inches long;
one (1) cup or eight (8) ounces of dried marigold and/or calendula leaves;
one (1) cup or eight (8) ounces of dried plantain weed; and
one (1) cup or eight (8) ounces of dried chickweed.
2. The topical skin healing salve of claim 1, wherein said raw beeswax, said white petroleum jelly or said castor bean jelly, and said raw unprocessed honeycomb and/or honey are heated in a cooking container until melted to a mixture, said yellow dock root, said yellow dock leaves, said marigold and/or calendula leaves, said plantain weed and said chickweed are added to said mixture in said cooking container, said mixture is simmered at a medium-low heat for sixty minutes or more and then said mixture is strained to remove debris therefrom and poured into one or more product containers to cool and solidify.

3. The topical skin healing salve of claim 1, wherein said beeswax, said white petroleum jelly or said castor bean jelly and said honeycomb and/or honey are melted into a mixture using heat and then the heat is lowered and said yellow dock root, said yellow dock leaves, said marigold and/or calendula, said plantain weed and said chickweed are added thereto and allowed to simmer.

4. The topical skin healing salve of claim 1, wherein said yellow dock root is finely chopped.

5. The topical skin healing salve of claim 1, wherein each of said marigold or said calendula, said plantain weed and said chickweed are firmly packed.

6. A topical skin healing salve, comprising:
one-half (0.5) pound raw beeswax;
twenty-six (26) ounces plain white petroleum jelly or castor bean jelly;
two (2) to three (3) tablespoons of raw unprocessed honeycomb and/or honey;
three (3) teaspoons of fresh yellow dock root;
twelve (12) to fourteen (14) fresh yellow dock leaves, each of said yellow dock leaves being approximately seven (7) to eight (8) inches long;
two (2) cups or sixteen (16) ounces of firmly packed fresh marigold and/or calendula leaves;
two (2) cups or sixteen (16) ounces of firmly packed fresh plantain weed; and
two (2) cups or sixteen (16) ounces of firmly packed fresh chickweed, wherein said raw beeswax, said white petroleum jelly or said castor bean jelly, and said raw unprocessed honeycomb and/or honey are heated in a cooking container until melted to a mixture and then said yellow dock root, said yellow dock leaves, said marigold and/or calendula leaves, said plantain weed and said chickweed are added to said mixture in said cooking container and then said mixture is strained to remove debris therefrom and then poured into one or more product containers to cool and solidify.

7. The topical skin healing salve of claim 6, wherein said mixture of said beeswax, said white petroleum jelly or said castor bean jelly, and said honeycomb and/or honey are heated until melted, the heat is lowered to a medium-low heat and said yellow dock root, said yellow dock leaves, said marigold and/or calendula, said plantain weed and said chickweed are added to said mixture, and then said mixture is allowed to simmer for one (1) hour.

8. A method of making topical skin healing salve, comprising the steps of:
(a) placing a mixture comprising one-half (0.5) pound raw beeswax, twenty-six (26) ounces plain white petroleum jelly or castor bean jelly and two (2) to three (3) tablespoons of raw unprocessed honeycomb and/or honey into a cooking container;
(b) applying heat to said mixture until said mixture is melted;
(c) lowering the heat to a medium-low and adding to said mixture one and one-half (1½) teaspoons of dried yellow dock root, six (6) to seven (7) dried yellow dock leaves each being approximately seven (7) to eight (8) inches long, one (1) cup or eight (8) ounces of dried marigold and/or calendula leaves, one (1) cup or eight (8) ounces of dried plantain weed, and one (1) cup or eight (8) ounces of dried chickweed;
(d) simmering said mixture for at least sixty minutes;
(e) straining said mixture to remove debris; and
(f) pouring said mixture into one or more product containers to cool and solidify.

9. The method of claim 8, wherein said yellow dock root is finely chopped in said adding step.

10. The method of claim 8, wherein each of said marigold or said calendula, said plantain weed and said chickweed are firmly packed in said adding step.

11. The method of claim 8, wherein said yellow dock leaves are crumpled in said adding step.

12. The method of claim 8, wherein said yellow dock root is finely chopped, each of said marigold or said calendula, said plantain weed and said chickweed are firmly packed and said yellow dock leaves are crumpled in said adding step.

13. The method of claim 8, wherein one or more of said yellow dock root, said yellow dock leaves, said marigold or said calendula, said plantain weed and said chickweed are fresh instead of dried and the quantity thereof is approximately doubled.

14. The method of claim 8, wherein each of said yellow dock root, said yellow dock leaves, said marigold or said calendula, said plantain weed and said chickweed are fresh and the quantity of each of said yellow dock root, said yellow dock leaves, said marigold or said calendula, said plantain weed and said chickweed is approximately doubled.

\* \* \* \* \*